(12) United States Patent
Amrane et al.

(10) Patent No.: US 11,046,704 B2
(45) Date of Patent: Jun. 29, 2021

(54) DERIVATIVES OF PORPHYRINS, THEIR PROCESS OF PREPARATION AND THEIR USE FOR TREATING VIRAL INFECTIONS

(71) Applicants: INSTITUT NATIONAL DE LA SANTE ET DE LA RECHERCHE MEDICALE (INSERM), Paris (FR); Centre national de la recherche scientifique, Paris (FR); UNIVERSITÉ DE BORDEAUX, Bordeaux (FR)

(72) Inventors: Samir Amrane, Pessac (FR); Marie-Aline Andreola, Bordeaux (FR); Geneviève Pratviel, Toulouse (FR); Jean-Louis Mergny, Pessac (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITÉDE BORDEAUX, Bordeaux (FR)

( * ) Notice: Subject to any disclaimer, the term of this patent is extended or adjusted under 35 U.S.C. 154(b) by 0 days.

(21) Appl. No.: 16/742,469

(22) Filed: Jan. 14, 2020

(65) Prior Publication Data
US 2020/0223858 A1    Jul. 16, 2020

Related U.S. Application Data

(62) Division of application No. 15/772,355, filed as application No. PCT/EP2016/076127 on Oct. 28, 2016, now Pat. No. 10,577,375.

(30) Foreign Application Priority Data

Oct. 30, 2015   (EP) .................................... 15306737

(51) Int. Cl.
| | | |
|---|---|---|
| *A61K 31/555* | (2006.01) | |
| *A61K 31/409* | (2006.01) | |
| *A61P 31/00* | (2006.01) | |
| *A61P 31/12* | (2006.01) | |
| *A61P 31/14* | (2006.01) | |
| *A61P 31/16* | (2006.01) | |
| *A61P 31/18* | (2006.01) | |
| *A61P 31/20* | (2006.01) | |
| *A61P 31/22* | (2006.01) | |
| *C07D 487/22* | (2006.01) | |
| *A61K 31/00* | (2006.01) | |

(52) U.S. Cl.
CPC ............ *C07D 487/22* (2013.01); *A61K 31/00* (2013.01); *A61K 31/409* (2013.01); *A61K 31/555* (2013.01); *A61P 31/00* (2018.01); *A61P 31/12* (2018.01); *A61P 31/14* (2018.01); *A61P 31/16* (2018.01); *A61P 31/18* (2018.01); *A61P 31/20* (2018.01); *A61P 31/22* (2018.01)

(58) Field of Classification Search
CPC ..... A61K 31/555; A61K 31/409; A61P 31/00; A61P 31/12; A61P 31/14; A61P 31/16; A61P 31/18; A61P 31/20; A61P 31/22
See application file for complete search history.

(56) References Cited

PUBLICATIONS

Dixon et al., Antiviral Chemistry & Chemotherapy, 1992, 3(5), pp. 279-282. (Year: 1992).*
Schickli et al., Human Vaccines, vol. 5, Issue 9, pp. 582-591, Sep. 2009. (Year: 2009).*
Al-Hazmi, Saudi Journal of Biological Sciences, 2016, 23, 507-511. (Year: 2016).*
Fehr et al., Coronaviruses: An Overview of Their Replication and Pathogenesis. Methods in Molecular Biology (Clifton, N.J.), 1282, 1-23, 2015. (Year: 2015).*

\* cited by examiner

*Primary Examiner* — Laura L Stockton
(74) *Attorney, Agent, or Firm* — B. Aaron Schulman, Esq.; Stites & Harbison, PLLC

(57) ABSTRACT

The present invention concerns metallated porphyrin derivatives as ligands of G-quadruplex and their novel use as anti-viral agents.

6 Claims, 4 Drawing Sheets

Specification includes a Sequence Listing.

DERIVATIVES OF PORPHYRINS, THEIR PROCESS OF PREPARATION AND THEIR USE FOR TREATING VIRAL INFECTIONS

CROSS-REFERENCE TO RELATED APPLICATIONS

This application is a divisional application of U.S. Ser. No. 15/772,355, having a filing date of Apr. 30, 2018, which was a 371 application of International application PCT/EP2016/076127 filed on Oct. 28, 2016, which claimed the benefit of European patent application EP 15306737.6, filed Oct. 30, 2015, all of said applications incorporated herein by reference.

The present invention concerns derivatives of porphyrins, their preparation and their application in therapeutics.

More specifically, this application is related to the use of porphyrin derivatives as G-quadruplex ligands to inhibit viral infections, such as HIV, more particularly to inhibit HIV-1 replication cycle.

Guanine rich RNA or DNA sequences are capable of folding and adopting four stranded structures called G-quadruplexes, or "G4" These unusual nucleic acid structures are based on the stacking of 2, 3 or 4 tetrads; each of which is composed of four guanines connected by 8 hydrogen bonds. These tetrads are stabilized by the presence of a central cation, $K^+$ or $Na^+$, abundantly present in the cellular environment, and which is coordinated with the oxygens of the carbonyl groups. Numerous thermodynamic studies have shown that these structures are very stable. They often have thermal denaturation temperatures above 50° C., and some are stable at 90° C. Once formed, some G4 such as the one formed by the c-myc promoter sequence, have a very long half-life and can withstand the annealing in the presence of high excess of their complementary strand (up to 50 times). Polymorphism, robustness and fast folding are some of the intrinsic characteristics of the G4 which strongly suggest a biological role.

Several bioinformatics studies have determined the distribution of quadruplex motifs in the human genome: i) The human genome has 370 000 potential quadruplexes motifs, ii) 40% of the genes encoding a protein have at least one quadruplex located at 1 kb from initiation site of the transcription, iii) important transcription factor binding sites, such as SP1, MAZ, Krox ZF5 are positioned near or overlap the G4 motifs, iv) 37% of the preferential recombination sites present a G4 motif. These correlations are conserved among different species in the evolution of the genomes.

Recently several in vivo studies have confirmed the existence of G4 in the genomic DNA and cellular RNA. Some studies have used fluorescent probes (antibodies or ligands) which specifically recognize G4s and do not bind to other DNA structures. These probes allowed the direct detection of G4s structures in immobilized chromosomes and confirmed the presence of quadruplexes in the regulatory regions of genes and subtelomeric regions. The involvement of G4s in replication, transcription, RNA splicing, or translation has also been extensively studied.

Quadruplexes have been identified as therapeutic targets, as follows:

a) Inhibition of Telomerase

Targeting G-quadruplexes was initiated in order to inhibit telomerase, a enzyme reactivated in 85% of cancers, but inactive in most normal cells. This enzyme recognizes the human telomeric sequence in its single-stranded conformation and maintains telomere length in tumor cells which makes them "immortal". The strategy is to stabilize telomeric G4s with chemicals to prevent telomerase interaction with its substrate. G4s ligands with anticancer properties have already been discovered, it is the case of Braco19, RHPS4 20 and 360A.

b) Inhibitions of Oncogenes

Many laboratories have been interested in quadruplex targeting to inhibit the expression of oncogenes. The oncogene c-myc is an important target of this approach: it has a G4 sequence in its promoter and the expression level of the gene depends on the formation of this structure. The formation of the G4 represses the transcription and this inhibition is enhanced in the presence of G4 ligands. The same type of repressive effect of the ligand was observed for KRAS, c-kit and bcl2 oncogenes.

c) Targeting G4s

The unique features of the G4 topology, very distinct from a DNA or RNA duplex or single-strand, make it a therapeutic target. G4s are compact structures which targeting can be likened to that of globular proteins. The great structural diversity of G4 suggests that a relatively high degree of selectivity can be achieved. Examples of rational design of ligands and in silico screening are becoming more numerous in the literature. This strategy opens a promising new era of targeting offering an alternative to the usual proteins targeting strategy. Furthermore, if the first applications were related only to cancer, new applications of this research are now considered in virology.

In a recent review, Harris et al proposed that the G4s may have a biological role in the life cycle of different pathogens (Harris & Merrick, *PLoS Pathog.* 2015 11(2):e1004562. The inventors also wrote a review describing the role of G4s in the replication cycle of many viruses (Métifiot et al *Nucleic Acid Res.* 2014 42, 12352-66). In the case of SARS coronavirus, a viral protein called "single domain SARS" (SUD) has two G4 binding sites. This viral protein seems essential for the virulence of the virus, would fight the immune response of the host by targeting the quadruplexes of the latter. In the case of Epstein-Barr virus EBNA1 viral protein binds to the G4 DNA and is involved in the viral replication cycle. Finally, HPV also presents G4 sequences in its genome.

The RNA genome of HIV-1 is changing very quickly, which gives it an important structural variability allowing it to escape the immune response of the infected organism. The low fidelity of the reverse transcriptase and the many genetic recombination events between the two viral RNAs are the drivers of this trend. These recombinations are facilitated by the dimerization of the viral RNA at the DIS sequence (Dimer Initiation Site). A recent study has suggested that this recombination could also be done via a bimolecular quadruplex using the cPPT sequences of each of the viral RNAs. In another study, a preferential recombination site was found at the 5' region of the gene gag. This guanine-rich sequence is capable of forming a bimolecular quadruplex with the homologous sequence on the other strand. This quadruplex facilitates the exchange of material between the donor RNA and the recipient RNA. NCp7 protein is known to facilitate the packaging of the viral RNA, the reverse transcription and integration into the genome, but is also able to open intramolecular RNA structures to promote the bimolecular structures. The NCp7 can also promote the formation of a bimolecular G4 with a receiver RNA.

Aptamers are nucleic acid sequences that can adopt a 3D structure and specifically recognize a given target. These structured nucleic acids are discovered by "SELEX" approaches. This is a method of in vitro selection from combinatorial libraries of synthetic oligonucleotides containing millions of different sequences. It is interesting to note that during the last fifteen years many aptamers adopting G4 structures were selected by this technique to target different HIV-1 proteins like the integrase, RT, gp120 and Rev. Some of these aptamers can prevent the entry of the virus into the cell by interacting with the viral protein gp120. Concerning integrase the 93del aptamer potentially binds to the catalytic pocket of the enzyme. This G4 strongly inhibits the infectivity of HIV-1 with an $IC_{50}$ of 25 nM. A functional study of the effects of this aptamer on the infectivity of HIV-1 in vivo conditions demonstrated that the fusion, transcription and integration of the provirus are inhibited by 93del. These studies show that certain viral proteins recognize very specifically and with high affinity the G4 structures.

In a previous application (EP14305763.6), the inventors showed that, despite its high genetic variability, HIV-1 genome presents several very conserved G4 forming sequences. These G4 sequences are associated with critical regulatory functions of the HIV replication cycle such as i) the initiation of reverse transcription by forming the central initiation point of the (+) strand synthesis by the reverse transcriptase; ii) the initiation of reverse transcription by forming the first point of (+) strand synthesis by the reverse transcriptase; iii) the regulation of the transcription of the provirus. The HIV virus was confronted to synthetic G4 DNA and RNA derived from its own genome. The observed inhibitory effects suggest that these synthetic "viral" G4s act as decoys diverting viral or cellular proteins from their natural targets in the viral genome.

US 2011/0064694 and US 2004/0116385 disclose porphyrin derivatives and their anti-viral activity. Porphyrin derivatives are disclosed inter alliae by Sabater et al., Dalton transactions (2015), 44(8), 3701-3707 and WO 200/27379. Perrone et al PLOSone 8, 8, e73121, 2013 discloses the antiviral effects of G-quadruplex binding in HIV.

According to a first object, the present invention concerns a compound of formula (I):

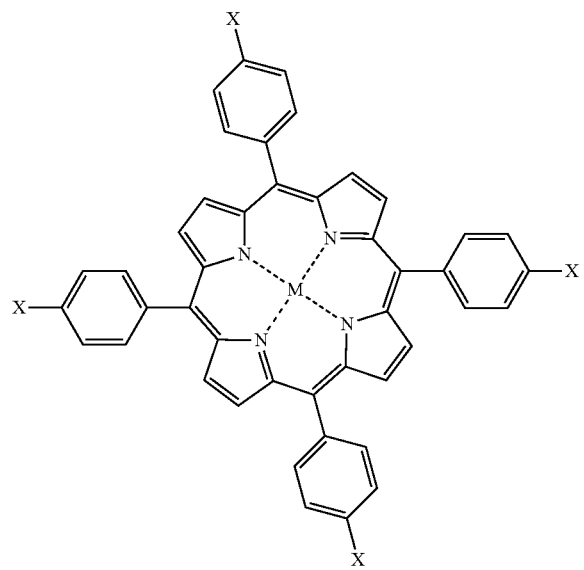

(I)

Where

X represents a group selected from:

a mono or bi cyclic 5 to 10 membered heteroaryl or heterocycle comprising at least one heteroatom chosen from N, O or S, optionally substituted by a group chosen from OH, O(C1-C6)alkyl, C1-C6 alkyl, Halogen, CN, $NO_2$, NRR';

a guanidine group of formula

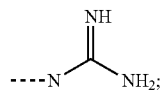

It being understood that X may be present in the form of an acid or base addition salt, R and R' identical or different independently represent a hydrogen atom or a group selected from C1-C6 alkyl, C6-C10 aryl, C3-C10 cycloalkyl, each alkyl, cycloalkyl and aryl being optionally substituted by one or more of OH, O(C1-C6)alkyl, C1-C6 alkyl, C6-C10 aryl, Halogen, CN, $NO_2$, . . . represents an optionally present single bond;

M is present or absent;

Where when . . . represents a single bond, M is present and represents a metal atom; together with a suitable counter ion, if appropriate, for its use in the prevention and/or treatment of a viral infection.

According to an embodiment, X represents a guanidinium group of formula

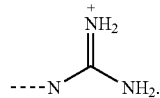

According to an embodiment, X represents an optionally substituted pyridine, such as a pyridine substituted by a C1-C6 alkyl, more particularly a methyl pyridinium.

Compounds H2-MA, Au-MA, Ni-PG, Au-PG, Mn-PG as depicted in FIG. 5 are particularly suitable for the use of the invention.

According to an embodiment, the present invention also concerns the use of a compound of formula (I) according to the invention for the preparation of a medicament for treating and/or preventing a viral infection.

According to a further embodiment, the present invention also concerns a method of treatment and/or prevention of a viral infection comprising the administration of a compound of formula (I) according to the invention as defined above to a patient in the need thereof.

Viral infections include all disorders caused by virus which comprise G quadruplex sequences in their genome at the DNA or RNA levels. Viral infections include in particular HIV, Epstein Barr virus, HPV, SARS coronavirus, Ebola virus and Marburg virus. According to an embodiment, the compounds of formula (I) are those of formula (IA), such as those of formula (I') or those of formula (I").

According to a further object, the present invention concerns compounds of formula (IA):

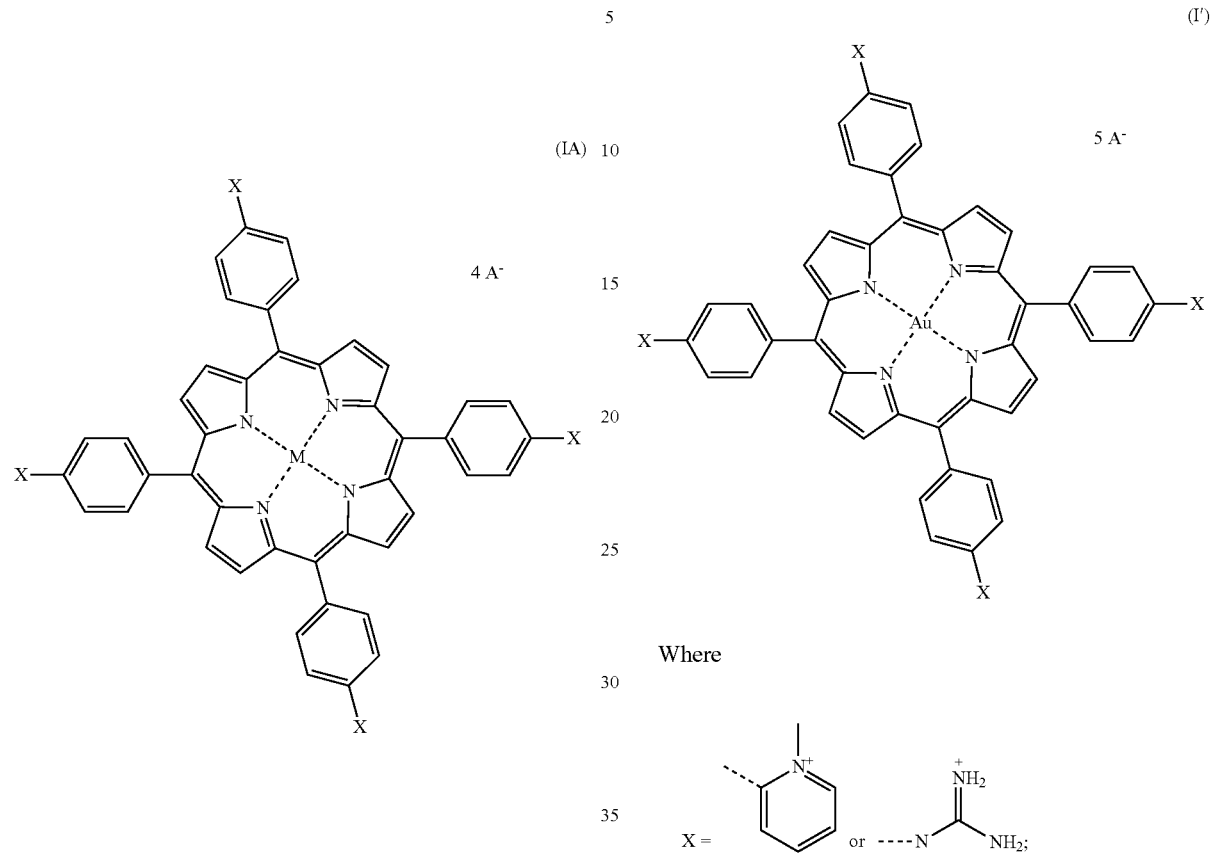

Where

A⁻ represents a counter anion;

M represents a metal atom, such as a gold atom (Au), cobalt atom (Co), Manganese (Mn) or a nickel (Ni) atom.

The present invention concerns in particular compounds H2-MA, Au-MA, Ni-PG, Au-PG, Mn-PG, more particularly Au-MA, Ni-PG, Au-PG, Mn-PG, as depicted in FIG. 5.

According to a specific object, the present invention concerns compounds of formula (I'):

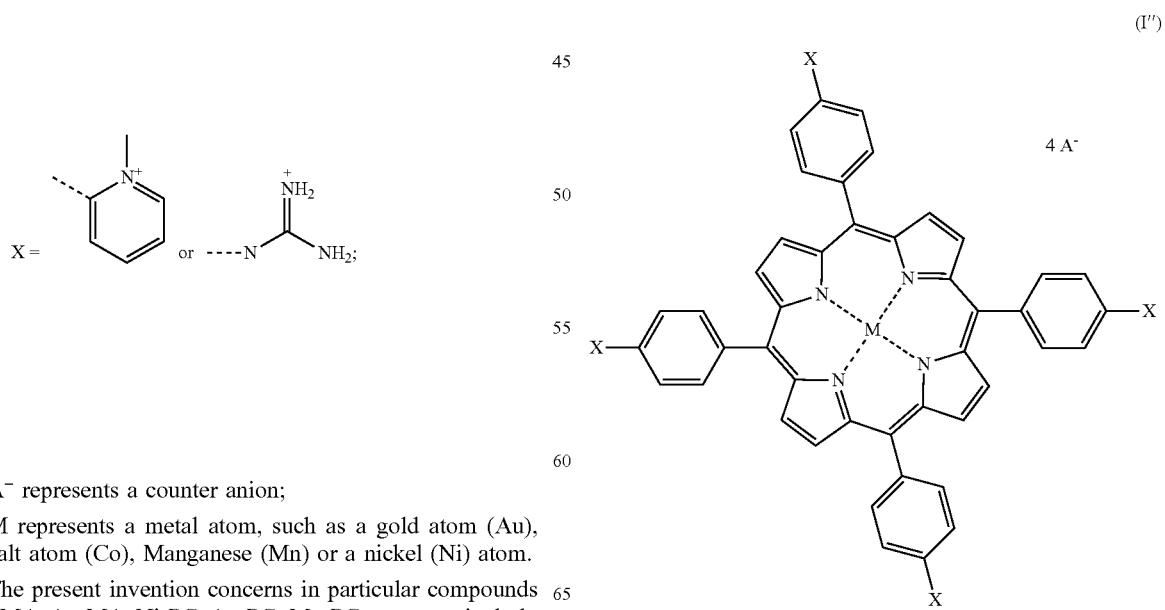

Where

A⁻ represents a counter anion;
Au represents a gold atom,
and compounds of formula (I''):

Where

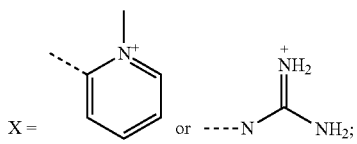

A⁻ represents a counter anion;
M represents a Co, Ni or Mn atom.

According to an embodiment, in formula (I), (IA), (I') or (I"), A⁻ represents an halogen ion, such as Cl⁻.

According to another object, the present invention concerns a pharmaceutical composition comprising a compound of formula (IA) such as (I') or (I") according to the invention as defined above, together with at least one pharmaceutically acceptable excipient.

Unless specified otherwise, the terms used hereabove or hereafter have the meaning ascribed to them below:

"Halo", "hal" or "halogen" refers to fluorine, chlorine, bromine or iodine atom.

"Alkyl" represents an aliphatic-hydrocarbon group which may be straight or branched having 1 to 6 carbon atoms in the chain. In a particularly preferred embodiment the alkyl group has 1 to 4 carbon atoms in the chain. Exemplary alkyl groups include methyl, ethyl, n-propyl, iso-propyl, iso-butyl, n-butyl, tert-butyl, n-pentyl, 3-pentyl.

"Cycloalkyl" refers to a non-aromatic mono- or polycyclic hydrocarbon ring system of 3 to 10 carbon atoms. More preferably the cycloalkyl group has of 4 to 10 carbon atoms, more preferably 4 to 8 carbon atoms and most preferably have 4 to 6 carbon atoms. Exemplary monocyclic cycloalkyl include cyclopropyl, cyclobutyl, cyclopentyl, cyclohexyl, cycloheptyl, and the like. Exemplary multicyclic cycloalkyl include 1-decalin, norbornyl, adamant-(1- or 2-)yl.

"Aryl" refers to an aromatic monocyclic or bicyclic ring containing 6 to 10 carbon atoms. Exemplary aryl groups include phenyl, naphthyl, indenyl, phenanthryl, biphenyl. Most preferably the aryl group is Phenyl.

The term "heteroaryl" refers to a 5 to 14, preferably 5 to 10 membered aromatic mono-, bi- or multicyclic ring wherein at least one member of the ring is a hetero atom such as N, O, S. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl.

The terms "heterocycle", "heterocyclyl" or "heterocyclic" refer to a saturated or partially unsaturated non aromatic stable 3 to 14, preferably 5 to 10-membered mono, bi or multicyclic rings wherein at least one member of the ring is a hetero atom, such as N, O, S. Typically, heteroatoms include, but are not limited to, oxygen, nitrogen, sulfur, selenium, and phosphorus atoms. Preferable heteroatoms are oxygen, nitrogen and sulfur. Suitable heterocycles are also disclosed in the *Handbook of Chemistry and Physics*, 76th Edition, CRC Press, Inc., 1995-1996, pages 2-25 to 2-26, the disclosure of which is hereby incorporated by reference. Preferred non aromatic heterocyclic include, but are not limited to oxetanyl, tetraydrofuranyl, dioxolanyl, tetrahydropyranyl, dioxanyl, pyrrolidinyl, piperidyl, morpholinyl, imidazolidinyl, pyranyl. Preferred saturated heterocycles are chosen from tetrahydrofuranyl, dioxolanyl, tetrahydropyranyl, dioxanyl, pyrrolidinyl, piperidyl, morpholinyl, imidazolidinyl, more preferably tetrahydrofuranyl, dioxolanyl, tetrahydropyranyl.

"metal" as used herein refers to Au, Ni, Mn, Co.

"Alkyl", "cycloalkyl", "aryl", etc. . . . also refers to the corresponding divalent "alkylene", "cycloalkylene", "arylene", etc., which are formed by the removal of two hydrogen atoms.

The compounds of formula (I) or (IA) such as (I') or (I") can be provided in the form of a free base or in the form of addition salts with acids, which also form part of the invention. The compounds of the present invention may possess an acidic group and a basic group which may form corresponding salts. Thus the present invention includes salts of compounds of formula (I) or (IA) such as (I') or (I"). The salts may preferably be pharmaceutically acceptable salts. The acidic group may form salts with bases. The base may be an organic amine base, for example trimethylamine, tert-butylamine, tromethamine, meglumine, epolamine, etc. The acidic group may also form salts with inorganic bases like sodium hydroxide, potassium hydroxide, etc. The basic group may form salts with inorganic acids like hydrochloric acid, sulfuric acid, hydrobromic acid, sulfamic acid, phosphoric acid, nitric acid etc and organic acids like acetic acid, propionic acid, succinic acid, tartaric acid, citric acid, methanesulfonic acid, benzenesulfonic acid, glucoronic acid, glutamic acid, benzoic acid, salicylic acid, toluenesulfonic acid, oxalic acid, fumaric acid, maleic acid etc. Further, compounds of formula (I) or (IA) such as (I') or (I") may form quaternary ammonium salts and salts with amino acids such as arginine, lysine, etc. Lists of suitable salts may be found in Remington's Pharmaceutical Sciences, 17th ed., Mack Publishing Company, Easton, Pa., 1985, p. 1418 and P. H. Stahl, C. G. Wermuth, *Handbook of Pharmaceutical salts—Properties, Selection and Use*, Wiley-VCH, 2002, the disclosures of which are hereby incorporated by reference.

These salts are advantageously prepared with pharmaceutically acceptable acids, but salts with other acids, useful for example for the purification or for the isolation of the compounds of formula (I) or (IA) such as (I') or (I"), also form part of the invention.

The compounds of formula (I) or (IA) such as (I') or (I") can comprise one or more asymmetric carbon atoms. They can therefore exist in the form of enantiomers or diastereoisomers. These enantiomers and diastereoisomers, as well as their mixtures, including racemic mixtures, form part of the invention.

It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

The compounds of formula (I) or (IA) such as (I') or (I") can also be provided in the form of a hydrate or of a solvate, i.e. in the form of associations or combinations with one or more water or solvent molecules. Such hydrates and solvates also form part of the invention.

According to another object, the present invention concerns the process of preparation of a compound of formula (IA) such as (I') or (I") according to the invention as defined above.

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, *Comprehensive Organic Transformations, VCH publishers,* 1989 The reagents and starting materials may be commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups herein named Pg may be used in accordance with standard practice, for examples see T. W. Greene and P. G. M. Wuts in Protective Groups in Organic Synthesis, John Wiley and Sons, 1991; J. F. W. McOmie in Protective Groups in Organic Chemistry, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethyl-formamide; alcohols such as ethanol and methanol and ethers, such as diethyl ether and tetrahydrofuran.

The reactions can take place over a wide range of temperatures. In general, it was found convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

In particular, the compounds of the present invention may be prepared from the processes described below.

According to the an embodiment, the process of the invention may comprise the step of reacting a compound of formula (II)

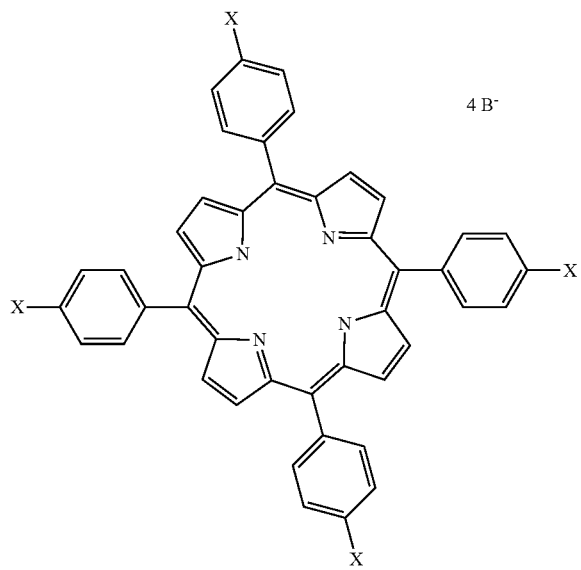

Where X is defined as in formula (I) (IA) such as (I') or (I") above,

Where B$^-$ represents a counter anion, such as trifluoroacetate

With a gold-containing complex, such as a complex of formula (III)

$$KAu^{III}A_4 \quad (III)$$

Where A$^-$ is a counter anion as defined in formula (I').

Generally, this step may be carried out in a suitable solvent such as a protic and polar solvent, such as water or acetic acid.

Typically, this reaction may be conducted at a temperature comprised between room temperature and the reflux temperature of the reaction mixture.

The process of the invention may further comprise the additional step of isolating, purifying and/or formulating the compound of formula (IA) such as (I') or (I") following coupling of compounds (II) and (III).

Generally, the compounds of formula (III) are commercially available or can be prepared by application or adaptation of known methods.

Compounds of formula (II) may be prepared according to Sabater et al., Dalton transactions (2015), 44(8), 3701-3707.

More specifically, the compounds of formula (II) may be obtained by either of the following pathways:

i) Where X represents a guanidine group: the compounds of formula (II) may be prepared by reacting a compound of formula (IV)

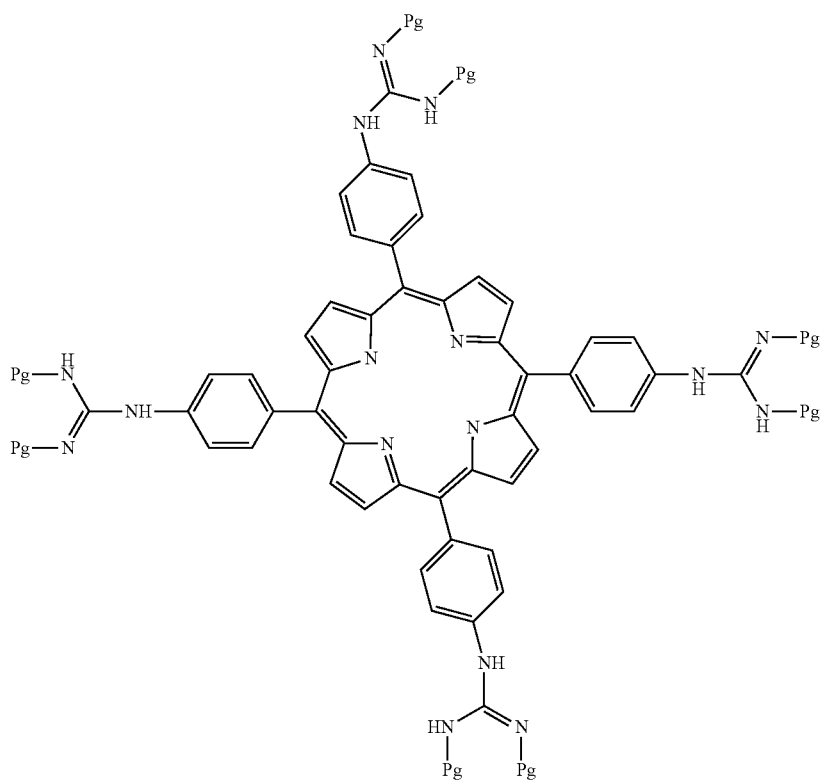

(IV)

Where Pg represents a protecting group of the amino group, such a Boc with the acid of formula (V):

H—B  (V)

Where B is defined as in formula (II).

Generally, this reaction may be carried out in an aprotic solvent, such as dichloromethane.

The compounds of formula (IV) may be obtained from the compound of formula (VI):

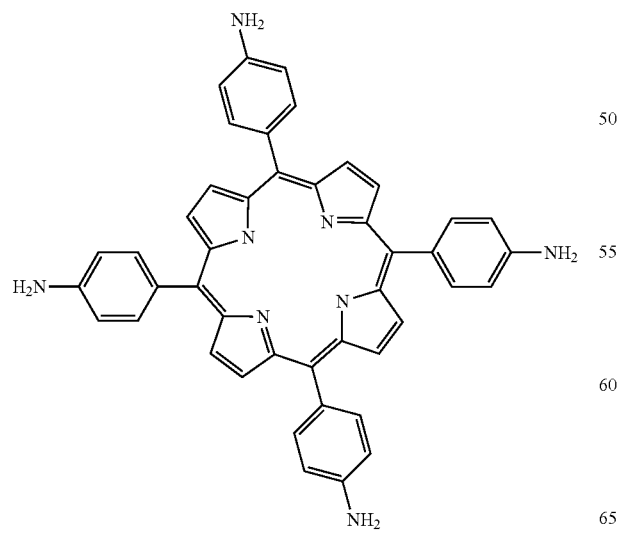

(VI)

With a compound of formula (VII):

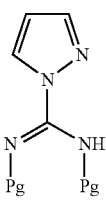

(VII)

Where Pg is defined as above.

This reaction may be conducted in a suitable solvent such as chloroform.

The porphyrin of formula (VI) is commercially available or may be prepared by application or adaptation of known procedures such as those disclosed by Bettelheim et al Inorg. Chem. 1987, 26, 1009-1017.

ii) Where X represents a methylpyridinium, the compound of formula (II) may be prepared by reacting a compound of formula (VIII)

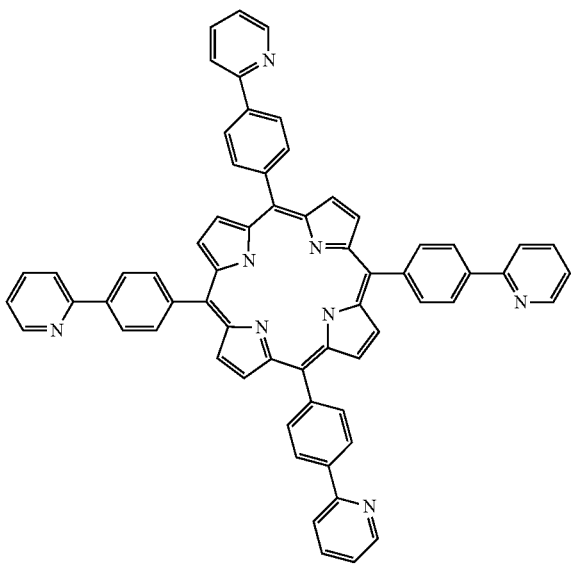
(VIII)

With a compound of formula (IX):

Hal—CH₃ (IX)

Where Hal represents typically I.

Generally, this reaction is followed by the addition of the acid H—B (V).

The coupling reaction may be conducted in a suitable solvent such as DMF or acetone or their mixture and may typically be conducted at a temperature comprised between room temperature and the reflux temperature of the reaction mixture.

The compound (VIII) may be obtained by reacting the compound of formula (X):

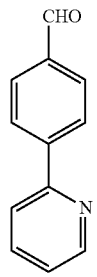
(X)

With a compound of formula (XI):

(XI)

in a solvent such as propionic acid, at a temperature comprised between room temperature and the reflux temperature of the reaction mixture.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, the expression "pharmaceutically acceptable" refers to those compounds, materials, compositions, or dosage forms which are, within the scope of sound medical judgment, suitable for contact with the tissues of human beings and animals without excessive toxicity, irritation, allergic response, or other problem complications commensurate with a reasonable benefit/risk ratio.

The dosage of drug to be administered depends on such variables as the type and extent of progression of the disease or disorder, the overall health status of the particular patient, the relative biological efficacy of the compound selected, and formulation of the compound, excipients, and its route of administration.

The compounds of present invention may be formulated into a pharmaceutically acceptable preparation, on admixing with a carrier, excipient or a diluent, in particular for oral or parenteral use. Oral preparations may be in the form of tablets, capsules or parenterals. A solid carrier can include one or more substances which may also act as flavoring agents, lubricants, solubilizers, suspending agents, fillers, glidants, compression aids, binders or tablet-disintegrating agents; it can also be an encapsulating material. Liquid carriers can include water, an organic solvent, a mixture of both or pharmaceutically acceptable oils and fats. The compositions may conveniently be administered in unit dosage form and may be prepared by any of the methods well known in the pharmaceutical art, for example, as described in Remington: The Science and Practice of Pharmacy, 20th ed.; Gennaro, A. R., Ed.; Lippincott Williams & Wilkins: Philadelphia, Pa., 2000. Pharmaceutically compatible binding agents and/or adjuvant materials can be included as part of the composition.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Preferred tablets contain lactose, cornstarch, magnesium silicate, croscarmellose sodium, povidone, magnesium stearate, or talc in any combination. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Other features of the invention will become apparent in the course of the following description of exemplary embodiments that are given for illustration of the invention and not intended to be limiting thereof.

DESCRIPTION OF THE FIGURES

FIG. 1: Effect of G4 ligands on G4 stability: The FRET melting experiments were performed in the presence of 0.5 µM of G4 ligand and using 0.2 µM of HIV-PRO sequence labelled with fluorophores.

FIG. 2: Effects of G4 ligands compared with AZT on HIV-1 infectivity using the HeLa P4 cell system for studying the replication of HIV-1. The HeLa P4 cells contain a gene lacZ encoding beta-galactosidase under the control of the viral LTR and whose transcription is activated by the viral protein Tat. The cells are incubated with the ligand then infected with HIV-1. After 24 hours the activity of beta-galactosidase, which is proportional to the infectivity of the virus is then measured on a fluorescence plate reader.

FIG. 3: Correlation between the apparent affinity of the ligands for the G4 (expressed in stabilisation of the G4 in ΔTm ° C.) and their inhibition activity on HIV.

FIG. 4: Measurement of the cell proliferation of HeLa cells as a function of time in the presence of increasing concentrations of Au-MA G4 ligand.

Figure 1:
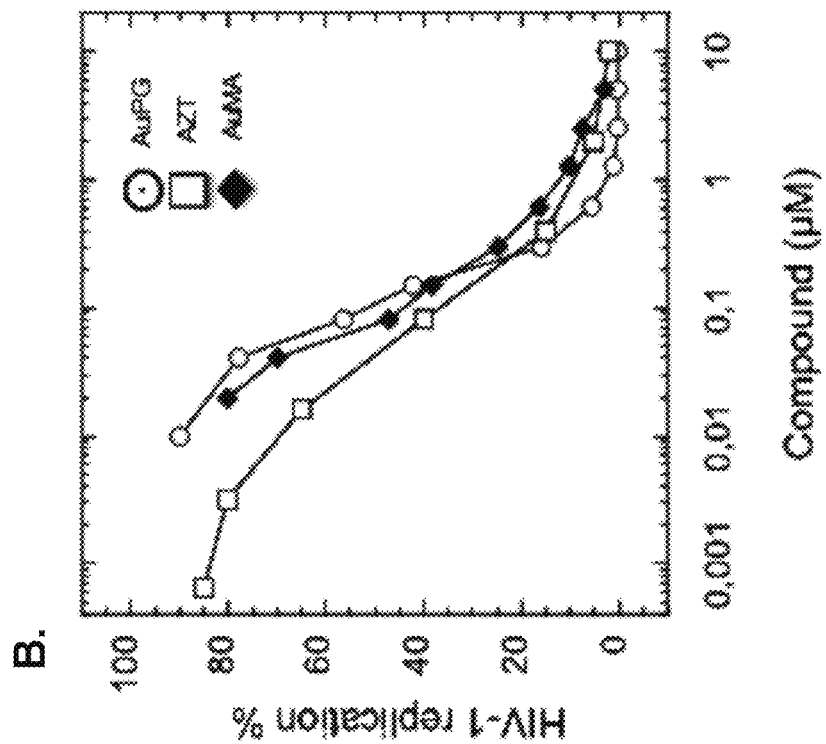
FIGS. 1 to 4 illustrate effect of the G4 ligands on HIV-1 replication.

The above mentioned features of the invention are given for illustration of the invention and not intended to be limiting thereof.

The following examples describe the synthesis of some compounds according to the invention. These examples are not intended to be limitative and only illustrate the present invention.

EXAMPLES

1. Synthesis of Compounds of Formula (I) or (IA)

1.1. [Preparation of meso-tetrakis(4-(N-methyl-pyridinium-2-yl)phenyl) porphyrinatogold(III) pentachloride] (Au-MA)

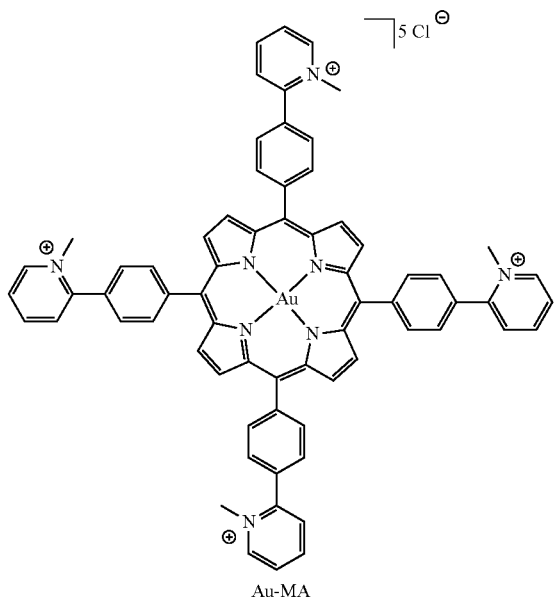

Au-MA

The synthesis of the non-metallated porphyrin was previously described in Sabater et al. *Dalton Trans.* 2015, 44, 3701.

Step 1: Synthesis of 5,10,15,20-tetrakis(4-(pyrid-2-yl)phenyl)porphyrin (1)

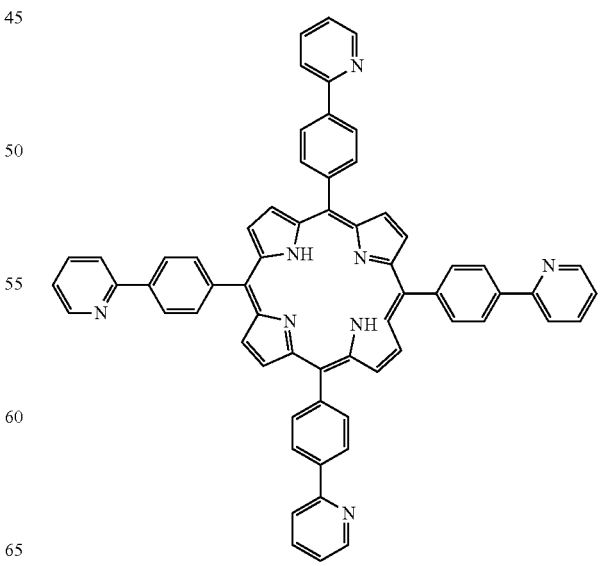

4-(Pyrid-2-yl)benzaldehyde (2.8 g, 15.3 mmol) was dissolved in propionic acid (72 mL), pyrrole (1 g, 15.6 mmol) was added and the mixture was refluxed for 1 h in the dark. The solvent was evaporated and the residue dried under vacuum. The crude product was taken in dimethyl formamide (50 mL) and filtered. The product was washed with dimethyl formamide (50 mL) and diethyl ether (2×50 mL) and dried under vacuum. Yield: 0.78 g (0.84 mmol, 22%) purple solid. $^1$H NMR (250 MHz, CDCl$_3$) δ=8.99 (s, 8H, pyrrole), 8.90 (d, J=5 Hz, 4H, pyridine), 8.44 (d, J=8 Hz, 8H, phenyl), 8.38 (d, J=8 Hz, 8H, phenyl), 8.10 (d, J=8 Hz, 4H, pyridine), 7.95 (ddd, J=8, 8, 1 Hz, 4H, pyridine), 7.40 (dd, J=8, 5 Hz, 4H, pyridine), −2.66 (s, 2H, NH). TLC Rf≈0.20 (SiO$_2$, CH$_3$CN/H$_2$O/KNO$_3$ sat. 8/1/1).

Step 2: Synthesis of 5,10,15,20-tetrakis(4-(N-methyl-pyridinium-2yl)phenyl)porphyrin tetrakis (trifluoroacetate) (2)

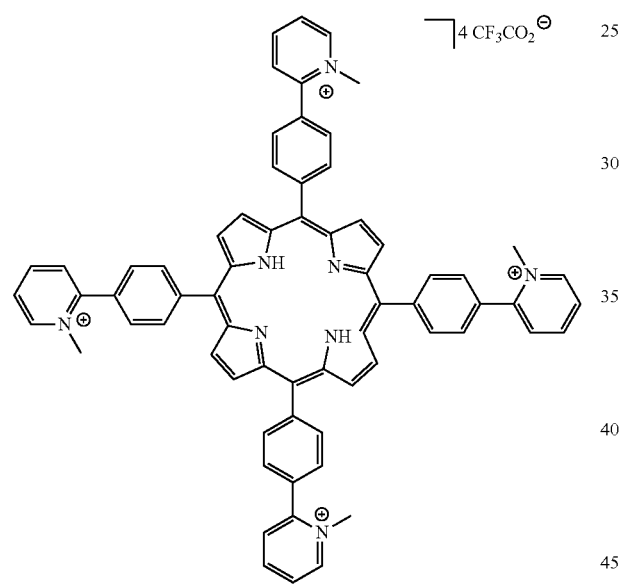

5,10,15,20-Tetrakis(4-(pyrid-2-yl)phenyl)porphyrin (1) (200 mg, 0.22 mmol) was dissolved in dimethylformamide (20 mL) and excess iodomethane (4 mL) was added. The mixture was heated at 155° C. for 3 h and acetone (100 mL) was added. The resulting purple precipitate was filtered off, washed with acetone, chloroform and diethyl ether. The product was purified on reverse phase C18 column (20 g), elution water with 0.1% TFA then water/acetonitrile, 80/20, v/v with 0.1% TFA. Yield: 210 mg (0.14 mmol, 66%) purple solid. $^1$H NMR (300 MHz, d$^6$-DMSO) δ=9.33 (d, J=6 Hz, 4H, pyridine), 9.04 (s, 8H, pyrrole), 8.84 (dd, J=8, 8 Hz, 4H, pyridine), 8.55 (d, J=8 Hz, 8H, phenyl), 8.48 (dd, J=8, 1 Hz, 4H, pyridine), 8.33 (ddd, J=8, 6, 1 Hz, 4H, pyridine), 8.19 (d, J=8 Hz, 8H, phenyl), 4.53 (s, 12H, CH$_3$-N), −2.83 (s, 2H, NH). UV-Vis (H$_2$O), λmax nm (ε M$^{-1}$ cm$^{-1}$) 416 (410×10$^3$), 516 (15×10$^3$), 552 (7×10$^3$), 580 (5×10$^3$), 634 (3×10$^3$). HRES$^+$-MS m/z: calculated for [C$_{68}$H$_{54}$N$_8$]$^{4+}$=245.6112, found: 245.6106. TLC Rf≈0.15-0.20 (SiO$_2$, CH$_3$CN/H$_2$O/KNO$_3$ sat. 8/1/1).

Step 3: 5,10,15,20-tetrakis(4-(N-methyl-pyridinium-2-yl)phenyl)porphyrinatogold(III) pentachloride (Au-MA)

Tetrakis(4-(N-methyl-pyridinium-2-yl)phenyl)porphyrin tetrakis(trifluoroacetate) (2) (30.5 mg, 0.021 mmol) was dissolved in water (10 mL). NaOH 1 M, 0.1 mL was added. KAu$^{III}$Cl$_4$ (11.4 mg, 0.030 mmol, 1.4 mol. eq.) was dissolved in water (1 mL) and added to the porphyrin solution. The mixture was refluxed for 24 h. The reaction was monitored by UV-visible spectroscopy and was stopped when the Soret band shift was complete (from 438 to 406 nm, in water, acidic pH). The reaction medium was cooled to room temperature. Desalting of the porphyrin was performed by reverse phase chromatography on a C18 Sep-Pak cartridge (5 g, Waters) by elution with water (200 mL) followed by methanol (20 mL). The collected fractions were evaporated to dryness and product taken in methanol/water, 50:50, v/v (20 mL). Anion exchange was performed on a DOWEX 1×8-200 resin column (chloride form, 1 g). The product solution was evaporated to dryness. The product was dissolved in methanol and precipitated by the addition of diethyl ether. After centrifugation the pellet was dried. Yield: 25.3 mg (0.0185 mmol, 88%) red solid. $^1$H NMR (400 MHz, CD$_3$OD) δ=9.61 (s, 8H, pyrrole), 9.26 (d, J=6 Hz, 4H, pyridine), 8.86 (dd, J=8, 8 Hz, 4H, pyridine), 8.66 (d, J=8 Hz, 8H, phenyl), 8.51 (d, J=8 Hz, 4H, pyridine), 8.32-8.27 (m, 12H, pyridine and phenyl), 4.66 (s, 12H, CH$_3$—N). UV-Vis (H$_2$O), λmax nm (εM$^{-1}$ cm$^{-1}$) 406 (400×10$^3$), 520 (21×10$^3$). ES$^+$-MS m/z=235.49 [M-5 Cl]$^{5+}$, 303.10 [M-4Cl]$^{4+}$, 415.80 [M-3Cl]$^{3+}$. TLC Rf≈0.24 (SiO$_2$, CH$_3$CN/H$_2$O/KNO$_3$ sat. 6/1/1).

1.2. [Preparation of 5,10,15,20-tetrakis(4-phenylguanidinium)porphyrinatogold(III) pentachloride] (Au-PG)

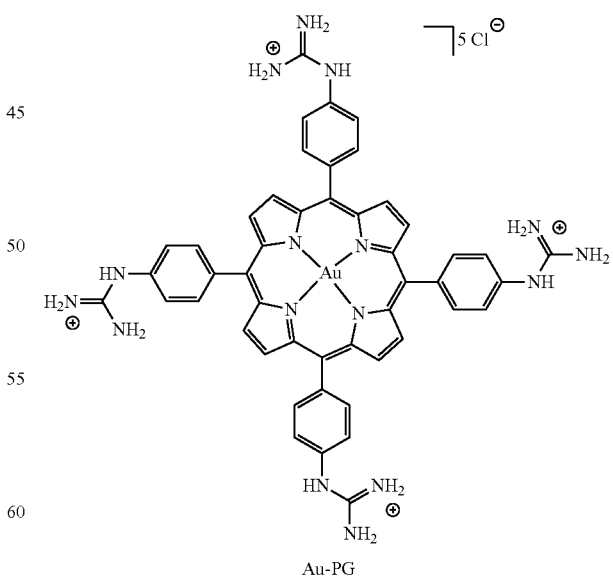

Au-PG

The synthesis of the non-metallated porphyrin was previously described in Sabater et al. *J. Biol. Inorg. Chem.* 2015, 20, 729.

Step 1: Synthesis of 5,10,15,20-tetrakis(4-(N,N'-ditertbutoxycarbonylphenylcarboxamidine)porphyrin (3)

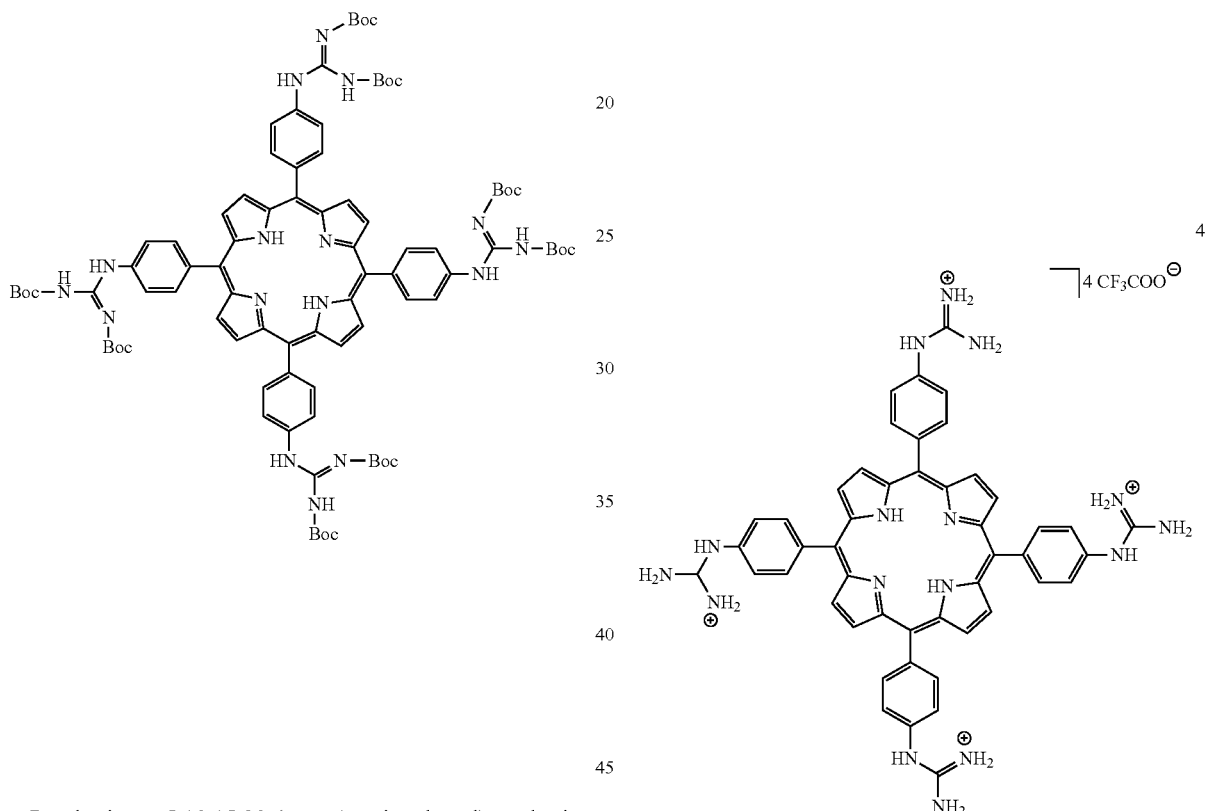

Porphyrin 5,10,15,20-(tetra-4-aminophenyl)porphyrin (502 mg, 0.74 mmol) and N,N'-bis(tertbutyloxycarbonyl)pyrazole-1-carboxamidine (1.2 g, 3.8 mmol) were dissolved in 15 mL of dry chloroform and the reaction mixture was stirred at room temperature, under argon, for 5-7 days while being monitored by TLC (SiO$_2$, diethyl ether). After removal of the solvent under reduced pressure, the product was purified by silica gel chromatography. The column was eluted with 250 mL of hexane/dichloromethane, 7/3, v/v with 1% triethylamine, followed by 500 mL hexane/dichloromethane, 6/4, v/v with 1% triethylamine, and 500 mL hexane/dichloromethane, 50/50, v/v, 1% triethylamine. The fraction of interest was dried under reduced pressure. The solid residue was washed with diethyl ether to ensure elimination of contaminating pyrazole derivative. Pure compound 3 was obtained as a purple solid (790 mg, 65%): Rf=0.7 (SiO$_2$, hexane/ethyl acetate, 7/3); $^1$H NMR (300 MHz, CDCl$_3$): δ=11.83 (s, 4H, N—H), 10.80 (s, 4H, N—H), 8.95 (s, 8H, pyrrole), 8.22 (d, J=8 Hz, 8H, phenyl), 8.09 (d, J=8 Hz, 8H, phenyl), 1.65 (s, 36H, CH$_3$), 1.61 (s, 36H, CH$_3$), −2.75 (s, 2H, N—H porphyrin); $^{13}$C NMR (75 MHz, CDCl$_3$): δ=163.67, 153.69, 153.50, 138.50, 136.75, 135.06, 131.23, 120.18, 119.60, 83.93, 79.88, 28.26, 28.18 ppm; HRMS-ES+m/z [M+H]+ calcd for C$_{88}$H$_{107}$N$_{16}$O$_{16}$: 1643.8051 (95%), 1644.8081 (100%), found: 1643.8074 (95%), 1644.8086 (100%). TLC Rf=0.7 (SiO$_2$, hexane/Et$_2$O 1/1).

Step 2: Synthesis of 5,10,15,20-tetrakis(4-phenylguanidinium)porphyrin tetratrifluoroacetate (4)

Porphyrin meso-5,10,15,20-tetrakis(4-(N,N'-ditertbutoxycarbonylphenylcarboxamidine)porphyrin (3) (800 mg, 0.49 mmol) was dissolved in 80 mL of dichlotomethane and reacted with 20 mL of trifluoroacetic acid under stirring for 3-4 h and the reaction mixture was evaporated under reduced pressure. The product was purified by dissolution in methanol followed by precipitation with diethyl ether. Precipitation procedure was repeated 4 times. The precipitate was filtered on a fritted glass, washed with diethyl ether to provide 4 as a microcrystalline purple solid (592 mg, 93%); $^1$H NMR (250 MHz, d$^6$-DMSO): δ=10.33 (s, 4H, N—H), 9.01 (s, 8H, pyrrole), 8.28 (d, J=8 Hz, 8H, phenyl), 7.87 (brs, 16H, N—H$_2$), 7.72 (d, J=8 Hz, 8H, phenyl), -2.90 (s, 2H, N—H porphyrin); HRMS-ES+m/z [M-4(CF$_3$CO$_2$)-3H]$^+$ calcd for C$_{48}$H$_{43}$N$_{16}$: 843.3857, found: 843.3873.

Step 3: 5,10,15,20-tetrakis(4-phenylguanidinium) porphyrinatogold(III) pentachloride (Au-PG)

Porphyrin meso-5,10,15,20-tetrakis(4-phenylguanidinium) porphyrin tetratrifluoroacetate (4) (50.2 mg, 0.039 mmol) was dissolved in acetic acid 10 mL. KAuCl$_4$ (53.0 mg, 0.014 mmol) was dissolved in water 2 mL and added to the porphyrin solution. The mixture was heated at 110° C. for 24 h. The reaction was monitored by UV-visible spectroscopy and was stopped when the Soret band shift was complete (Soret band of the the metallated derivative at 408 nm in acidic water). After evaporation to dryness the product was taken in water/methanol, 80/20, v/v and the medium was centrifuged. The supernatant was loaded on a reverse phase C18 Sep-Pak cartridge (5 g, Waters). Elution with water (200 mL) was followed by methanol (20 mL) and then methanol containing 0.5% trifluoroacetic acid. The collected fractions were evaporated to dryness and product taken in methanol/water, 50/50, v/v (20 mL). Anion exchange was performed on a DOWEX 1×8-200 resin column (chloride form, 1 g). The product solution was evaporated to dryness. The product was dissolved in methanol (5 mL) and precipitated by the addition of diethyl ether (20 mL). After centrifugation the pellet was washed with diethyl ether and dried. Yield: 28.6 mg (0.023 mmol, 60%) red solid. $^1$H NMR (400 MHz, CD$_3$OD): δ=9.54 (s, 8H, pyrrole), 8.41 (d, J=8 Hz, 8H, phenyl), 7.87 (d, J=8 Hz 8H, phenyl). UV/vis (H$_2$O): λmax nm (ε M$^{-1}$ cm$^{-1}$) 408 (285×10$^3$). ES$^+$-MS m/z=346.9 [M-2H-5Cl]$^{3+}$, 260.2 [M-H-5Cl]$^{4+}$.

2. Biological Activity 2.1. Methods

A. Preparation of the oligonucleotides:

Fluorescent oligonucleotides were purchased from Eurogentec (Seraing, Belgium) with "Reverse-Phase Cartridge Gold purification". Concentrations were determined by ultraviolet (UV) absorption using the extinction coefficients provided by the manufacturer. All oligonucleotides were dissolved in 20 mM potassium phosphate buffer pH7 containing 70 mM KCl.

B. FRET melting experiments:

The HIV-PRO sequence (5'TGGCCTGGGCGGGACTGGG3') (SEQ ID No 1) was labelled with fluorescein at the 5'end and TAMRA at 3'end. The transfer of fluorescence energy between fluorescein and tetramethylrhodamine is only possible when the two fluorophores are close in the folded state at low temperature. In the unfolded state at high temperature, the FRET is reduced. The fluorescence melting profiles were recorded on a Stratagene quantitative PCR device (De Cian A, et al. Fluorescence-based melting assays for studying quadruplex ligands. Methods. 2007 June; 42(2):183-95.).

C. Cell lines and viruses: HeLa P4 cells encoding a Tat-inducible β-galactosidase were maintained in DMEM medium (Invitrogen) supplemented with 10% inactivated FCS, 1 mg/ml geneticin (G418, Gibco-BRL), gentamycin. MT4 and H9LaI cells were grown in RPMI 1640 glutamax medium (Invitrogen) supplemented with 10% inactivated FCS. HIV-1 viruses were obtained after 48 h co-culture of MT4 cells (0.5×106/ml) and H9Laï cells (1×106/ml), chronically infected by HIV-1LaI isolate, in RPMI 1640 glutamax medium supplemented with 10% inactivated FCS, at 37° C. under humidified atmosphere and 5 CO2. The culture was then centrifuged and the supernatant was clarified by filtration on a 0.45 μm membrane before freezing at −80° C.

D. Viral infectivity test: The G4 ligands are incubated in presence of the HelaP4 cells 20 minutes before infection. The infectivity was assayed on HeLa P4 cells expressing CD4 receptor and the β-galactosidase gene under the control of the HIV-1 LTR. HeLa P4 were plated using 200 μl of DMEM medium supplemented with 10% inactivated FCS in 96-multi-well plates at 10 000 cells per well. After overnight incubation at 37° C., under humidified atmosphere and 5% CO2, the supernatant was discarded and 200 μl of viral preparation were added in serial dilutions. After 24 h of infection, the supernatant was discarded and the wells were washed 3 times with 200 μl of PBS. Each well was refilled with 200 μl of a reaction buffer containing 50 mM Tris-HCl pH 8.5, 100 mM β-mercaptoethanol, 0.05% Triton X-100 and 5 mM 4-methylumbelliferyl-B-D-galactopyranoside (4-MUG) (Sigma). After 24 h, the reaction was measured in a fluorescence microplate reader (Cytofluor II, Applied Biosystems) at 360/460 nm Ex/Em.

E. Cytotoxicity study of the G4 ligands: HeLa, human epithelial carcinoma cell line and Wi38, normal human fibroblast cell line were used as experimental model to assess cellular proliferation in the presence of G4 ligands. Cells have been seeded in 384-well plates. All measures have been performed in duplicates in one experiment. The cell proliferation was measured as the surface of the well occupied by the cells. A proliferation index was then calculated by making a ratio on the surface occupied at the time-point preceding the treatment. The cell count is also assessed at the last time-point of the kinetics. Cytolysis Lyzed cells are stained with a nuclear marker, able to enter only cells with compromised membranes. The number of lyzed cells per well is reported all along the kinetics. For the last time-point of the kinetics, a percentage of cytolysis is also computed after getting the maximum cytolysis for each well by permeabilizing cells.

2.2. Results: Specific G4 Ligands Inhibits HIV-1 Replication

2.2.1. G-Quadruplex Ligands

As part of the anti-cancer strategies described above, a wide variety of quadruplex ligands have been developed. These molecules are very good G4 specific structural probes. They bind very little to double-stranded and single-stranded DNA but recognize very well all types of G4 with dissociation constants in the order of tens to hundreds of nano-molar. The ability of some ligands (for instance XM14 and Br-360A) to bind to HIV-PRO3 sequence was evaluated using a stabilization test by FRET (FIG. 1). 3 different families of G4 ligands were used: Salfens, Bisquinoliniums and porphyrins. This technique allows to select molecules which bind to HIVPRO labelled with fluorophores. In this test, thermal denaturation experiments were performed followed by fluorescence and measure the fluorescence emission of fluorescein. Ligand binding to the fluorescent oligonucleotide stabilizes the structure and these results in an increase in the temperature of half-dissociation of the latter (FIG. 1). The more the $T_m$ increases, the larger is the affinity of the ligand for the target. Thus, in the example shown, the ligand 360A further stabilizes the G4 as compared to XM14 compound; its affinity for the G4 is higher. These experiments were also performed in the presence of a duplex competitor composed of 26 base pairs (data not shown). Thus, the binding selectivity of the ligand for the G4 in competition with the duplex can be evaluated. If the stabilization is maintained in the presence of 50 molar equivalents of non-fluorescent competitor duplex (600 equivalents when comparing the number of base pairs to the number of G4 tetrads), the ligand is considered to be selective, but if the stabilization disappears, the ligand is considered not very selective, and this is the case for three porphyrins (H2PYMA, AUT and Tmpyp4). 43 ligands were tested, 23 were selected from the three different chemical families that have interesting affinity and specificity features to study their inhibitory effects on HIV.

2.2.2. Inhibition of HIV

Figure 2:
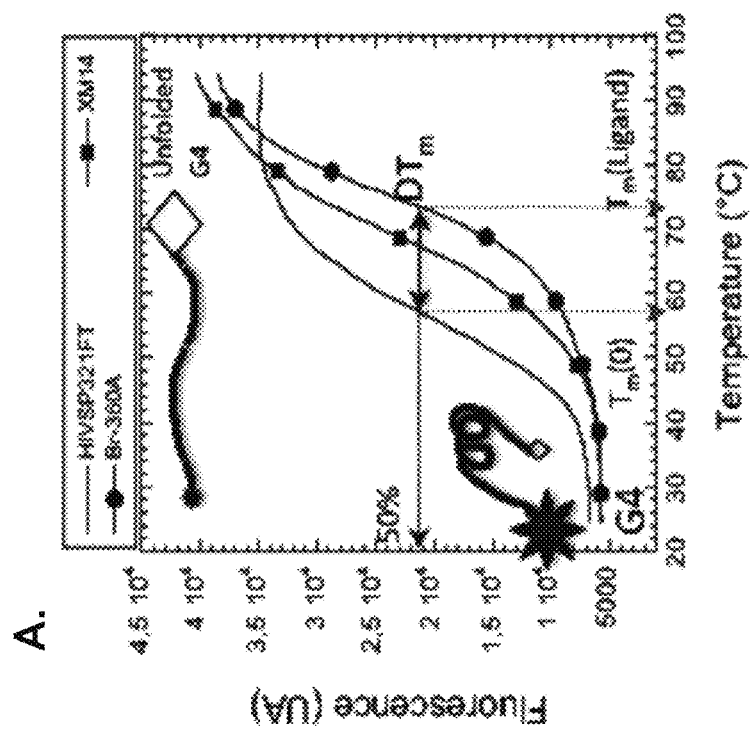
Figure 3:
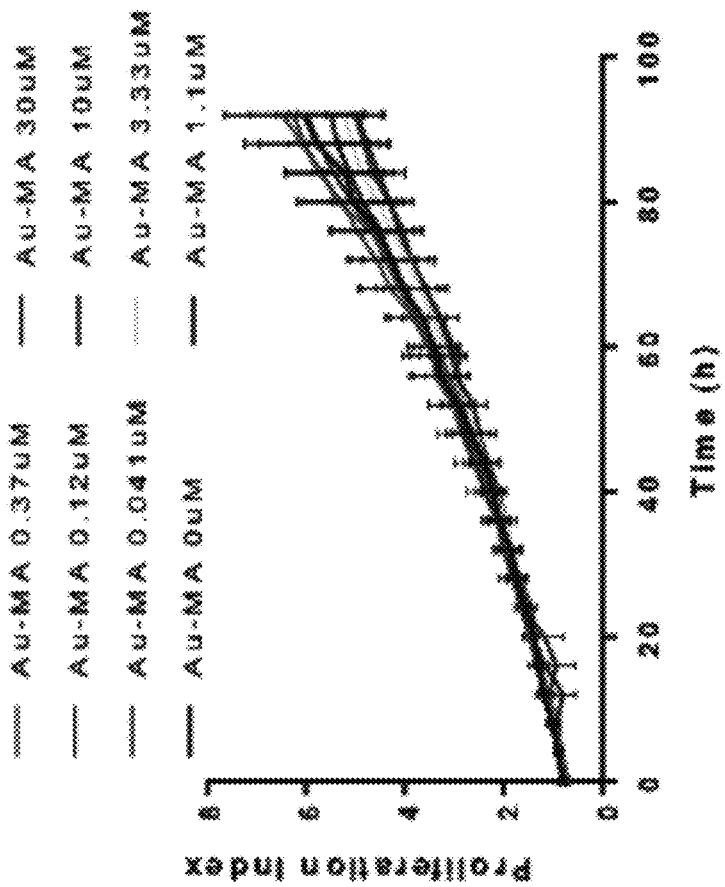
Figure 4:
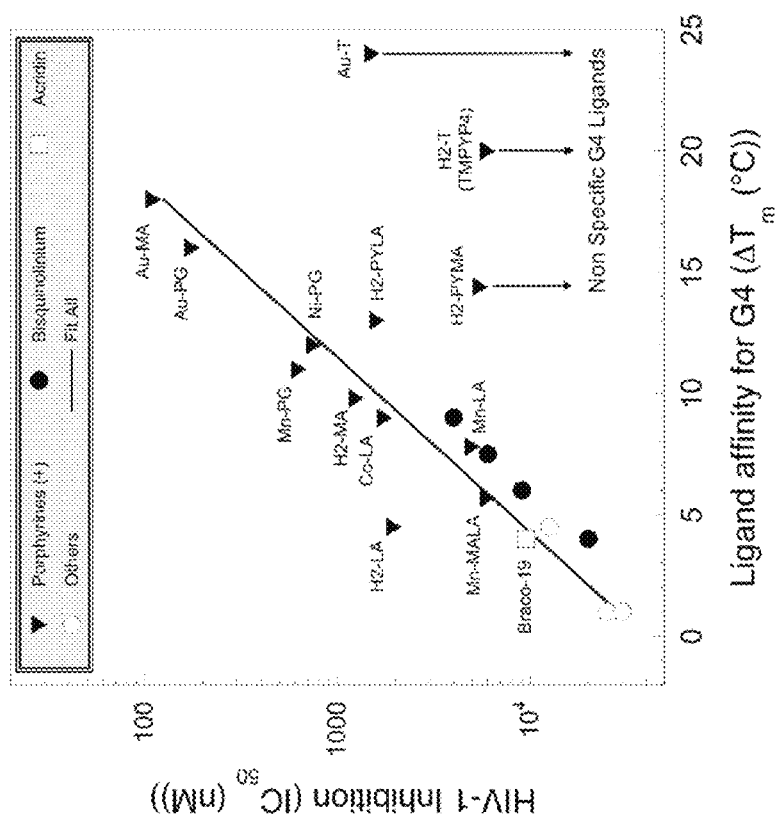
Figure 5:
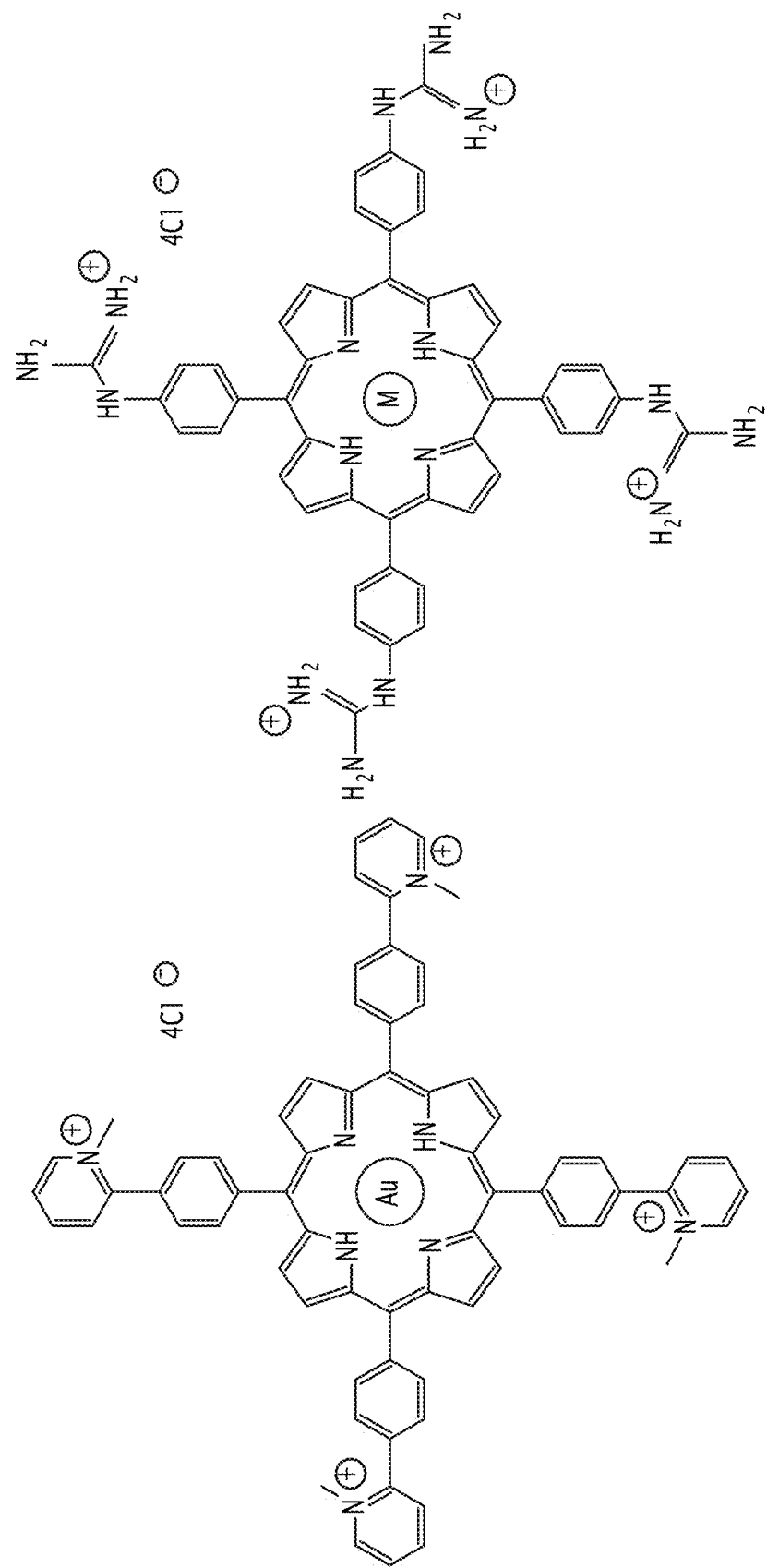
FIG. 5 represents the structure of the compounds of the invention that are tested and illustrated in FIG. 3. X=H2 refers to the case where no metal is in the center (M is absent).
Figure 6:
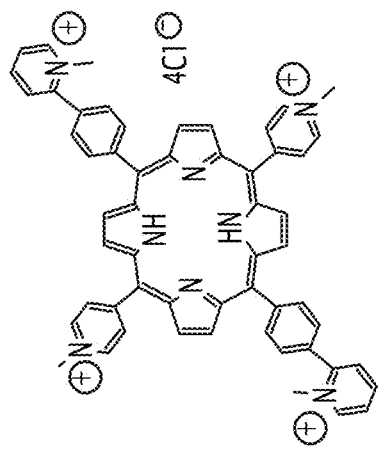
FIG. 6 represents the structure of comparative prior art compounds that are tested and illustrated in FIG. 3. X=H2 refers to the case where no metal is in the center (M is absent).
Figure 6:
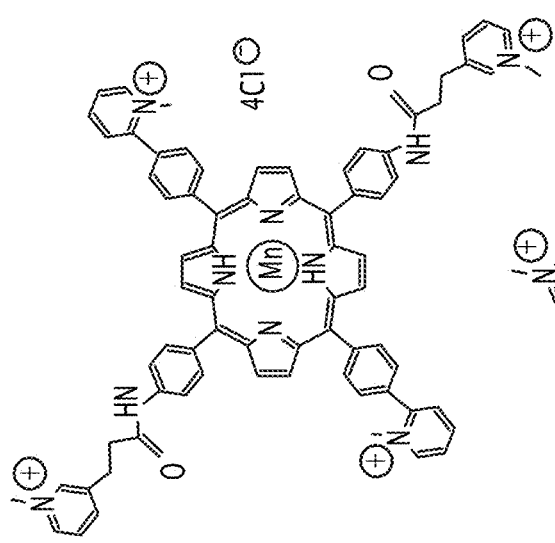
Figure 6:
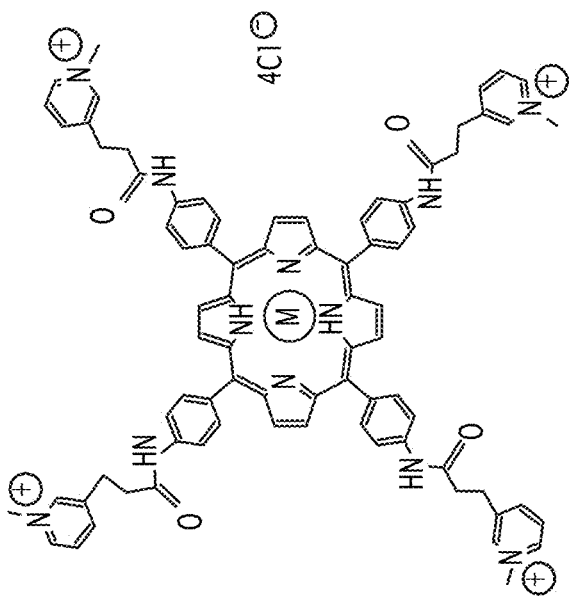
Figure 6:
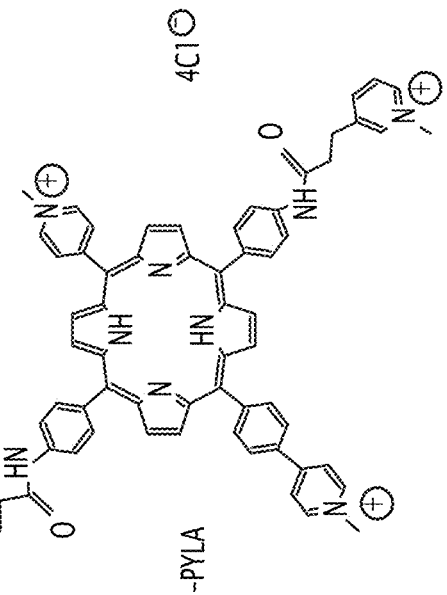
Figure 6:
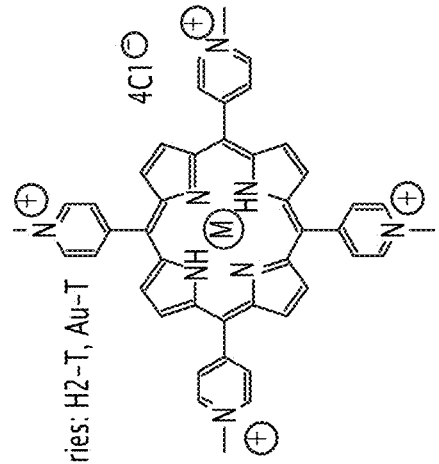

The next step was therefore to test the effect of these ligands on the viral replication (FIG. 2) and see if there is a correlation between the ability to stabilize the G4 in vitro ($\Delta T_m$) and the effect on viral infectivity in cellulo (FIG. 2). By testing these 23 ligands, it was shown that there is a significant correlation between the affinity of a ligand for the G4, whatever its chemical or structural nature (Bisquinolinium, porphyrins and Salen) and its inhibitory potential (FIG. 2). An increase of G4 stabilization by 7° C. directly translates in an $IC_{50}$ which is divided by 10. Compounds in the LA, MALA, T, PYLA and PYMA series are porphyrins derivatives disclosed in the literature and are tested as a comparative examples. The best compounds are porphyrin derivatives according to the invention of the Ma and PG series having an $IC_{50}$ of around 100 nM. Under the same conditions, AZT has an inhibitory effect just below with an $IC_{50}$ of 40 nM. For H2PYMA, AUT and Tmpyp4 G4 ligands, the competition FRET experiments demonstrated that they were much less specific to the G4 structures. These compounds also bind to duplex and single-stranded DNA. They turned out to be weak inhibitors of viral replication. The low efficiency was interpreted by the "dilution" on non-specific targets. Cytotoxicity test on KB cells, A549, MCF7, MRC5, HCT116 and HeLa P4 showed no cytotoxic effect of these ligands on a period of 92 h and a concentration of up to 30 µM (FIG. 4). This correlation between stabilization in vitro and in vivo inhibition (FIG. 3), associated to the high specificity of these ligands, and the absence of cytotoxicity on human cells, suggest that the observed inhibition is due to the recognition of quadruplex structures of the virus in the viral RNA or DNA.

What is claimed is:

1. A method for the treatment of a viral infection selected from the group consisting of viral infections caused by viruses for which G4 forming sequences are directly or indirectly involved in the infection process, said method comprising administering a compound of formula (I):

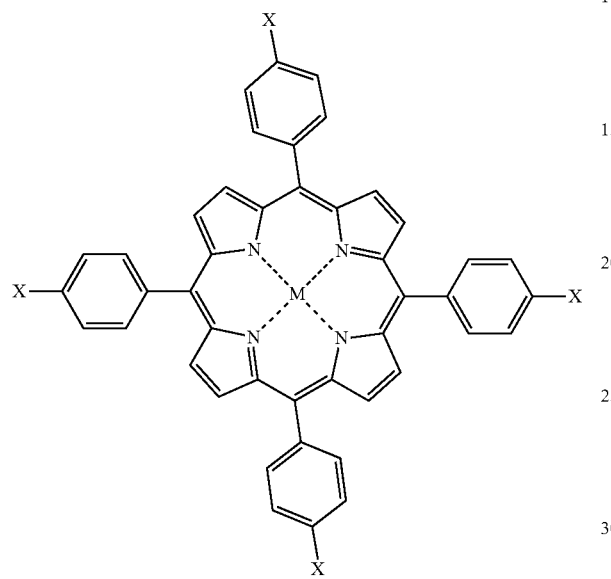

(I)

where
X is selected from the group consisting of:
  a mono 6 membered heteroaryl or heterocycle comprising at least one heteroatom selected from the group consisting of N, O, and S, optionally substituted by a group selected from the group consisting of OH, O(C1-C6)alkyl, C1-C6 alkyl, halogen, CN, NO$_2$, and NRR'; and
  a guanidine group of formula

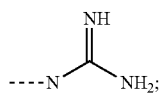

wherein X may be present in the form of an acid or base addition salt,
R and R' identical or different independently represent a hydrogen atom or a group selected from the group consisting of C1-C6 alkyl, C6-C10 aryl, and C3-C10 cycloalkyl, each alkyl, cycloalkyl or aryl being optionally substituted by one or more of OH, O(C1-C6)alkyl, C1-C6 alkyl, C6-C10 aryl, halogen, CN, or NO$_2$,
. . . represents an optionally present single bond;
M is present or absent;
where when . . . represents a single bond, M is present and represents H$_2$ or a metal atom;
together with an optional counter ion when appropriate, to a patient in the need thereof.

2. The method according to claim 1, where the viral infection is selected from the group consisting in HIV, Ebola virus, and Marburg virus.

3. The method according to claim 1, where the viral infection is HIV.

4. The method according to claim 1, where the compound of formula (I) is of formula (IA):

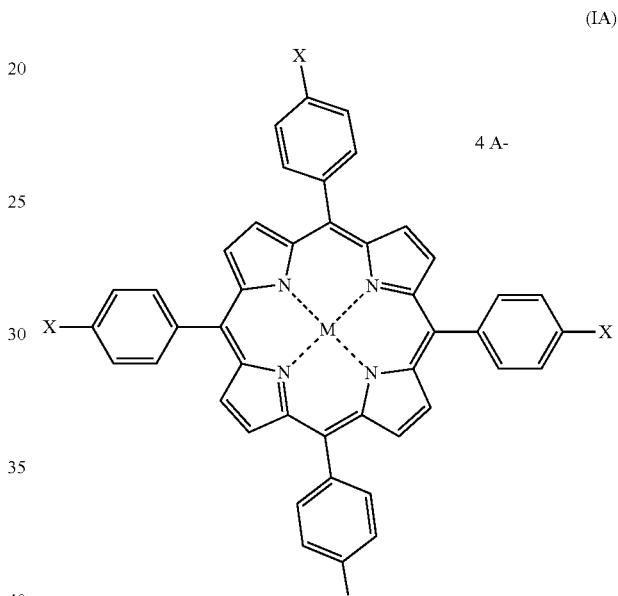

(IA)

where

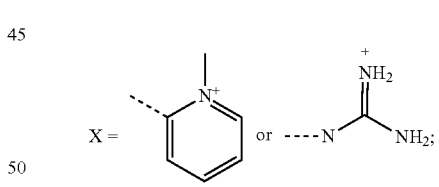

A$^-$ represents a counter anion;
M represents H$_2$, a gold atom (Au), cobalt (Co), Manganese (Mn) or a nickel (Ni) atom.

5. The method according to claim 4, where A$^-$ represents a halogen ion.

6. The method according to claim 4, where A$^-$ is Cl$^-$.

* * * * *

SEQUENCE LISTING

<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: probe

<400> SEQUENCE: 1
tggcctgggc gggactggg                                                  19